(12) United States Patent
Mizuta et al.

(10) Patent No.: US 8,243,134 B2
(45) Date of Patent: Aug. 14, 2012

(54) OPTICAL READER CAPABLE OF CHANGING THE INCIDENT ANGLE OF DARK FIELD ILLUMINATION

(75) Inventors: Takahisa Mizuta, Gamagori (JP); Hidetomo Sakiyama, Gamagori (JP)

(73) Assignee: Kowa Company Ltd. (JP)

( * ) Notice: Subject to any disclaimer, the term of this patent is extended or adjusted under 35 U.S.C. 154(b) by 524 days.

(21) Appl. No.: 12/461,782

(22) Filed: Aug. 21, 2009

(65) Prior Publication Data

US 2010/0045807 A1  Feb. 25, 2010

(30) Foreign Application Priority Data

Aug. 22, 2008  (JP) ................. 2008-213833

(51) Int. Cl.
*H04N 7/18* (2006.01)
*G06K 7/10* (2006.01)

(52) U.S. Cl. ......... 348/131; 348/126; 382/147; 235/455

(58) Field of Classification Search .......... 348/125–126, 348/128, 131, 373, 375
See application file for complete search history.

(56) References Cited

U.S. PATENT DOCUMENTS

| | | | | | |
|---|---|---|---|---|---|
| 5,455,870 | A | * | 10/1995 | Sepai et al. | 382/147 |
| 5,737,122 | A | * | 4/1998 | Wilt et al. | 359/436 |
| 5,933,521 | A | * | 8/1999 | Pasic | 382/145 |
| 6,667,762 | B1 | * | 12/2003 | Bouvier et al. | 348/92 |
| 2004/0165759 | A1 | * | 8/2004 | Baldwin | 382/141 |
| 2005/0087601 | A1 | * | 4/2005 | Gerst et al. | 235/455 |
| 2007/0153084 | A1 | * | 7/2007 | Deveau et al. | 348/126 |

* cited by examiner

*Primary Examiner* — Ngoc-Yen Vu
(74) *Attorney, Agent, or Firm* — Adams & Wilks

(57) ABSTRACT

An optical reader includes an imaging device and an photographing optical system for reading images of an object such as a semiconductor wafer. An LED light source is provided as a dark field illumination light source for illuminating the object at an angle of illumination that deviates from the optical axis of the photographing optical system. The LED light source is supported by a swing-type support member having both ends secured to a housing of the optical reader using screws and nuts. This allows the angle and position of the dark field illumination light source to be adjusted so as to provide a first angle of illumination for illuminating the object directly with the illuminating light from the dark field illumination light source, or a second angle of illumination for illuminating the object by reflection from a half mirror that is disposed in an illumination optical system.

6 Claims, 3 Drawing Sheets

OPTICAL READER CAPABLE OF CHANGING THE INCIDENT ANGLE OF DARK FIELD ILLUMINATION

BACKGROUND OF THE INVENTION

1. Field of the Invention

The present invention relates to an optical reader, and in particular to an optical reader having an imaging device and a photographing optical system for reading images of an object.

2. Description of the Prior Art

Images that are obtained with optical microscopes or semiconductor inspection devices vary greatly depending on how the object is illuminated (differences in amount of light, wavelength, and angle of incidence). Differences in image are directly related to image scanning or inspection performance and reliability. Dark field illumination is an important illumination means for making minute objects easier to see or for improving processing efficiency in OCR or other applications.

Dark field illumination light sources are intended to illuminate objects at an angle of illumination that doesn't coincide with the optical axis of the photographing optical system. An illumination optical system including a ring-slit reflection component is used to illuminate an object from the peripheral direction thereof for dark field illumination (see Japanese Patent 3445722). Furthermore, optical readers are known in which light-emitting diodes (LED) are disposed with certain directional characteristics, i.e., are disposed in a pattern around the optical axis for use as ring illumination.

Semiconductor wafers are also an example of objects that are scanned by this type of optical reader. For example, this type of optical reader is sometimes used when symbols marked on a mirror-like surface are scanned for an OCR process or the like. Dark field illumination is also effective for applications such as the defect inspection of lenses or glass sheets. The illumination angle of the illuminating light may be important, but vary depending on the depth of the markings or defects, substances deposited above and around them or background thereof. Deposited substances may include oxide films, nitride films, or polyimides, and examples of background include circuit patterns.

As mentioned above, directional characteristics are required of dark field illumination light sources, and there is thus a need for dark field illumination devices that are capable of illumination at various angles to deal with defects/markings that vary in depth. In OCR optical systems which are used for wafer marking recognition, there is a need for an optical system that would be flexibly adaptable, since illumination angles of incidence suitable for a variety of wafer models would significantly enhance the recognition efficiency of individual wafer markings.

In optical readers for reading semiconductor wafer markings, characters and the like, an illumination light source of LEDs may be disposed at locations allowing the object to be illuminated at a desired angle of incidence in order to deal with defects/markings of various depths. In such cases, dark field illumination light sources must be disposed at multiple locations when illumination at multiple angles of incidence is required.

The general usability of a device will be expanded if the types of incident angles of dark field illumination are increased, but a resulting problem is that the number of illumination light sources is increased, and more space is needed for the light sources, thereby leading to devices of greater size and greater manufacturing costs. Furthermore, when the configuration of the dark field illumination is made variable, it is sometimes necessary to change the position of the illumination light source and change the direction of the illumination light source. Unless suitably constructed, the range within which the illumination light source can be moved will be limited, or the size of the device and the costs might possibly be needlessly increased.

SUMMARY OF THE INVENTION

It is therefore an object of the present invention to provide an optical reader being capable of changing the incident angle of dark field illumination in various ways corresponding to the characteristics of an object for improvement in visibility of captured images and image processing efficiency.

According to the present invention, an optical reader has an imaging device and a photographing optical system for reading images of an object, and comprises a dark field illumination light source for illuminating the object at an angle of illumination that deviates from the optical axis of the photographing optical system; reflection means for reflecting the illuminating light from the dark field illumination light source in the direction of the object; and adjustment means for adjusting the angle and position of the dark field illumination light source so as to provide either a first angle of illumination for directly illuminating the object with the illuminating light of the dark field illumination light source, or a second angle of illumination for illuminating the object by reflection via the reflection means.

In the present invention, the reflection means is disposed in an illumination optical system that is disposed near the photographing optical system and includes an illumination light source different from the dark field illumination light source.

The illumination optical system that includes an illumination light source different from the dark field illumination light source is a bright field illumination optical system, or it includes a bright field illumination light source and a low-angle dark field illumination light source.

The low-angle dark field illumination light source comprises a first low-angle dark field illumination light source in which the angle of incidence with the optical axis is 1° to 3°, and a second low-angle dark field illumination light source in which the angle of incidence with the optical axis is 3° to 5°.

In the present invention, an optical reader further comprises means for adjusting the angle of reflection of the reflection means.

According to the present invention, the illuminating light from the dark field illumination light source can be adjusted by the adjustment means to obtain either a first angle of illumination for illuminating the object directly or a second angle of illumination for illuminating the object by reflection via the reflection means. A broad range of angles of incidence can thus be selected for the dark field illumination light source while minimizing increases in the size of the device and manufacturing costs compared to structures in which numerous dark field illumination light sources having different directions of illumination are arranged. It is also possible to improve the efficiency of imaging processes such as OCR processes.

An illumination optical system includes a reflecting means that is jointly used as the reflection means that provides the second angle of illumination. In particular, the illumination optical system can be constructed, for example, as a bright field illumination optical system.

The illumination optical system is provided with a low-angle dark field illumination optical system with different angles of illumination. Means for adjusting the reflection angle of the reflection means can also be provided to allow the illumination angles of the low-angle dark field illumination optical system to be adjusted to select dark field illumination angles within a more diverse range of angles.

The above-mentioned means for adjusting the reflection angle of the reflection means also allows dark field illumination angles of the dark field illumination light source to be adjusted within a greater range of angles.

Further features of the invention, its nature and various advantages will be more apparent from the accompanying drawings and following detailed description of the invention.

DESCRIPTION OF THE PREFERRED EMBODIMENTS

The present invention will now be described in detail based on the illustrated embodiments. The embodiments are described with reference to an optical reader capable of reading semiconductor wafer markings or defects.

Figure 1:
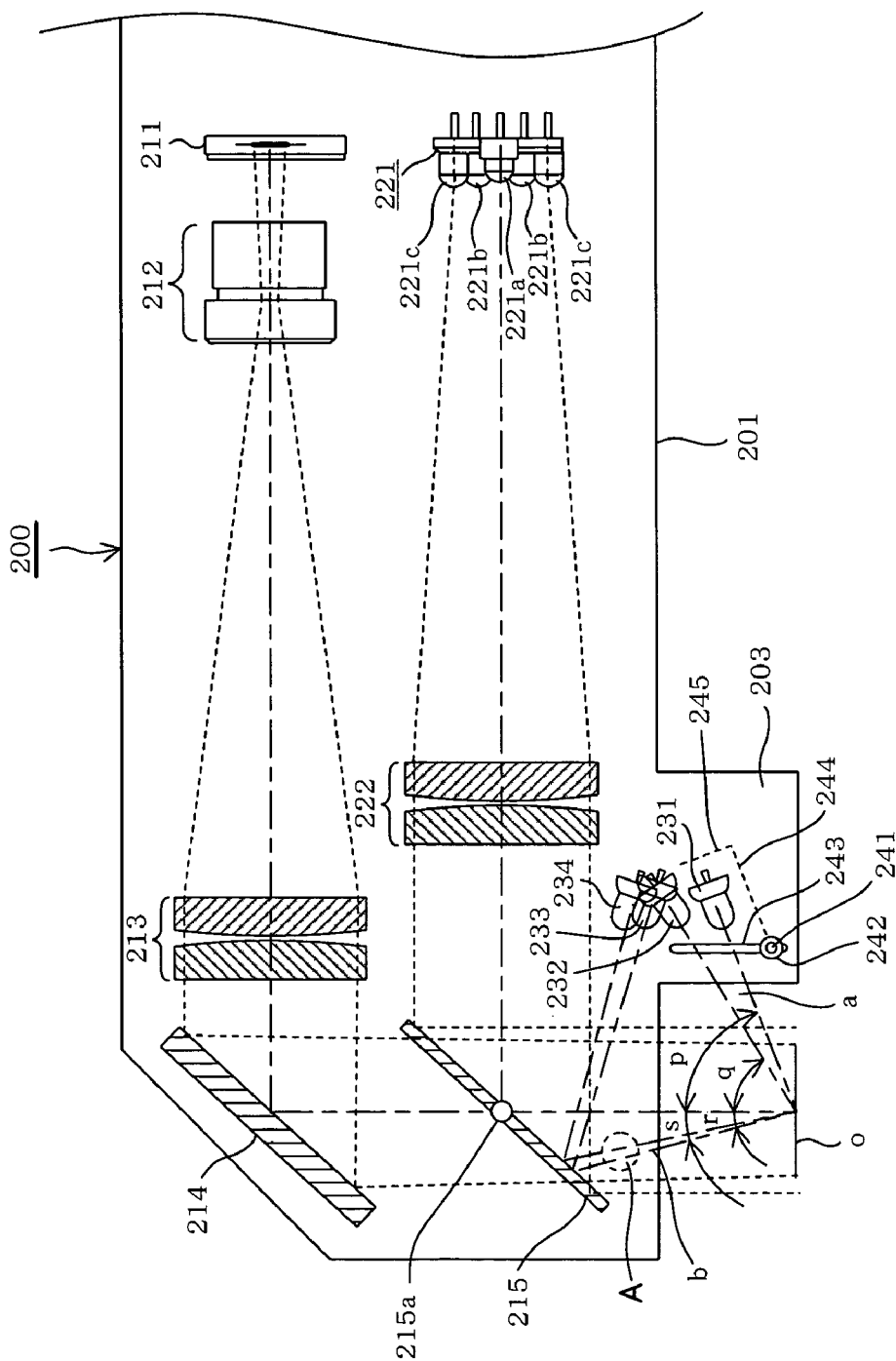
FIG. 1 is a schematic view showing the structure of an optical reader according to the present invention.

FIG. 1 shows the main structure of the photographing optical system and illumination optical system of an optical reader 200 according to the present invention. In FIG. 1, reference numeral 201 indicates the frame of the optical reader 200. The photographing optical system and illumination optical system are housed in the interior of the frame 201, which is composed of a plastic or metallic material, and is substantially L-shaped.

The photographing optical system includes an imaging device 211 that is composed of a CCD or CMOS sensor or the like, in front of which is disposed an optical system composed of a front lens assembly 213 and a rear lens assembly 212. A total reflection mirror 214 is disposed in front of the front lens assembly 213 to vertically orient the optical axis of the photographing optical system.

The output of the imaging device 211 is transmitted to an image processing circuit (not shown), and the resulting image is displayed on a display (not shown), or subjected to an OCR process in order to read the markings, characters and the like of an object O such as a semiconductor wafer.

The illumination optical system comprising both bright field illumination and dark field illumination is disposed under the photographing optical system. The illumination optical system includes a light source of an LED 221 composed of an LED array made of several LED light sources, for example. The LED 221 is composed of three illumination light sources: a bright field illumination light source 221a that is disposed so as to be substantially coaxial with the illumination optical axis; a low-angle dark field illumination light source 221b having a first angle of incidence such as 20 (ranging from 1° to 3°); and a low-angle dark field illumination light source 221c having a second angle of incidence such as 30 (ranging from 3° to 5°) A condenser lens 222 is disposed in front of the LED 221. The illumination light converted to nearly parallel light is reflected by a half mirror 215 that is disposed under the total reflecting mirror 214. In particular, the optical axis of bright field illumination light from the bright field illumination light source 221a is oriented vertically downward so as to be substantially coaxial with the optical axis of the photographing optical system.

However, the LED 221 may include just the bright field illumination light source 221a to provide a bright field illumination optical system via the half mirror 215.

In this embodiment, the half mirror 215 is also used as reflection means for reflecting the illumination light to the direction of the object O from a dark field illumination light source (LED 231) that will be described below.

The half mirror 215 is rotatably supported by a spindle 215a disposed in a direction intersecting with the optical axis, for example, and can be fixed at any angle of rotation within a range of 1 to several degrees, for example, using a mechanism that is not shown. This is used for the purpose of adjusting the illumination angle of the illumination light from the above-mentioned low-angle dark field illumination light sources 221b and 221c. The half mirror 215 may also be designed so that its angle can be rapidly returned to the initial position by a notch mechanism or the like (not shown) in order to make the optical axis of the bright field illumination properly coaxial with the optical axis of the photographing optical system.

A housing 203 protrudes from the underside of the frame 201 under the bright field illumination optical system in order to accommodate the dark field illumination optical system.

Figure 2:
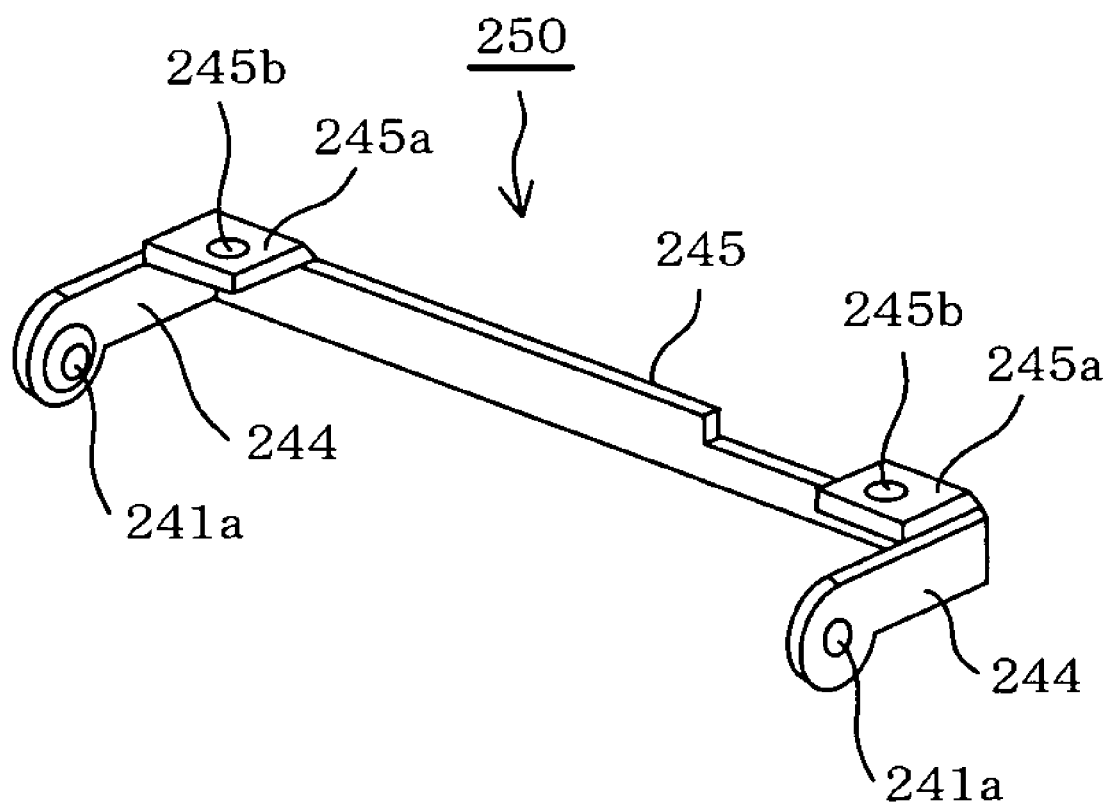
FIG. 2 is a perspective view showing the structure of the support member for the LED in the optical reader of FIG. 1.
Figure 3:
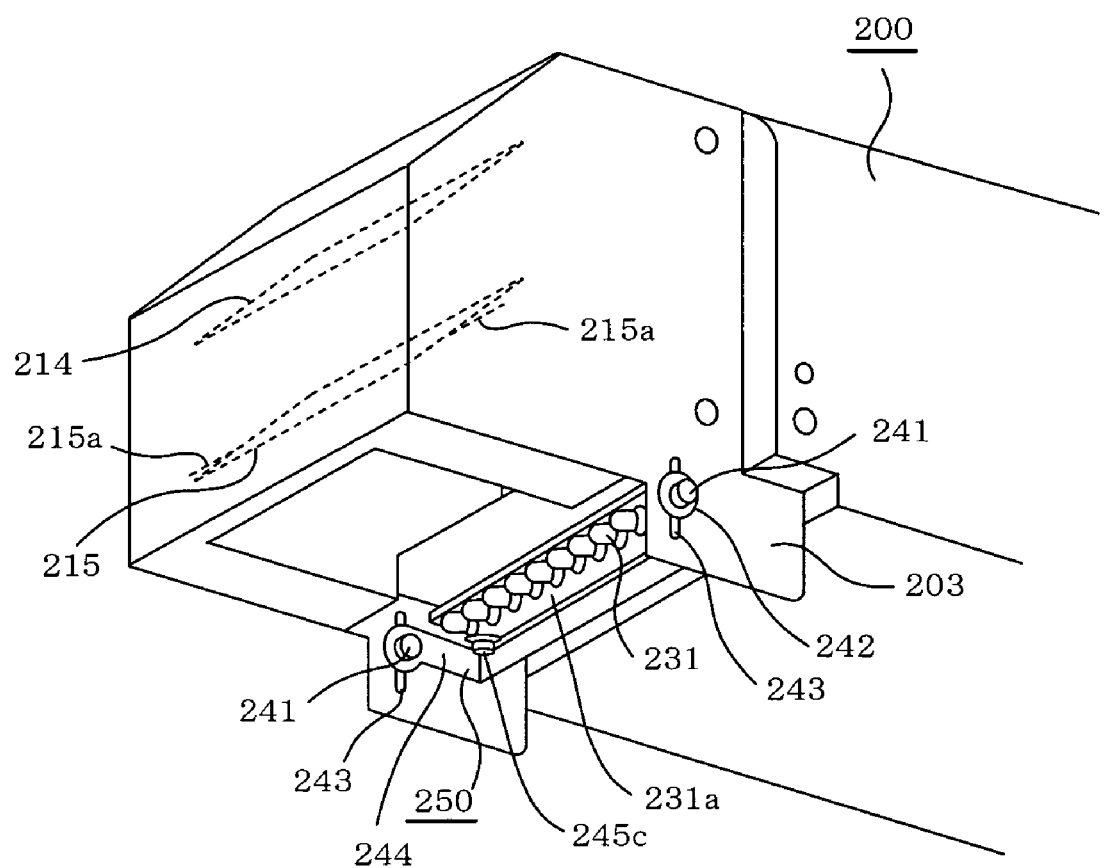
FIG. 3 is a perspective view showing the structure of the main parts of the optical reader of FIG. 1.

The housing 203 can be formed by extending the left and right side panels of the frame 201 as shown in FIG. 3, for example, and an LED 231 as the dark field illumination light source is supported between the left and right side panels by a swing-type support member 250, as shown in FIG. 2.

The dark field illumination light source of the LED 231 is used to illuminate an object at an angle of illumination that doesn't coincide with and deviates from the optical axis of the photographing optical system.

The support member 250, as shown in FIG. 2, has a support component 245 between the left and right arms 244, 244, and has, at the corners of the support component 245, support panels 245a and 245a for supporting a base plate on which the LED 231 is arranged. These structures can be formed, for example, using a process for bending metal panels or plastic casting.

Multiple LEDs 231 are arranged on a base plate 231a, as shown in FIG. 3. Although the LEDs 231 are arranged in line in FIG. 3, the pattern in which the LEDs 231 are arranged is not limited to the illustrated pattern, and may be arranged as desired by a person skilled in the art. The LEDs 231 may be provided with light projection heads having directional characteristics in the distal direction by using a type of element in which the projection head has been fabricated in the form of a lens.

The base plate 231a is fixed by left and right screws 245c (right side not shown in FIG. 3) to the tap holes 245b and 245b of the support panels 245a and 245a located at the corners of the support member 250.

Through holes 241a and 241a are provided in the distal ends of the arms 244, 244 of the support member 250. As shown in FIG. 1 and FIG. 3, the support member 250 is fixed by the screws 241 and 241 and nuts 242 and 242 to long holes 243 and 243 in the left and right side panels of the housing 203.

In the present embodiment, the nuts 242 and 242 are shown as simple ring-shaped parts, but their circumference may be knurled to prevent slippage, wing nuts may be used, or another scheme may be adopted to facilitate manual loosening and tightening.

According to the above structure, the nuts 242 and 242 and the screws 241 and 241 can be loosened to rotate the support member 250 (shown by the dashed line in FIG. 1) and thereby change the angle of the dark field illumination of the LEDs 231 serving as the dark field illumination light source. The support member 250 can also be moved vertically along the long holes 243 and 243 to thereby adjust the position. Even though the angle of the dark field illumination is thus changed, the optical axis of the LED 231 can be adjusted by vertical movement so as not to be displaced from the position where the optical axis of the photographing optical system intersects the object O.

In FIG. 1, the symbols 232, 233, and 234 show the orientation of illumination by the LED 231 which can be selected by the rotation of the support member 250 and its vertical movement along the long holes 243 and 243.

Rotation and its vertical movement of the support member 250 along the long holes 243 and 243, the length and position of the long holes 243 and 243 or the length of the arms 244, 244 of the support member 250 are set so as to allow the object O to be illuminated directly by the LED 231, as shown by symbols 231 and 232, or to allow the object O to be illuminated by reflection of light from the LED 231 via the half mirror 215, as shown by symbols 233 and 234.

In this way, the angle of the dark field illumination for the object O can be selected as either a first illumination angle a for directly illuminating the object O by the LED 231, or a second illumination angle b for illuminating the object O by reflection from the half mirror 215. The first illumination angle a and second illumination angle b can be micro-adjusted through micro-adjustment of the angle of the arms 244, 244 of the support member 250, and the fixing position thereof relative to the long holes 243, 243. For example, in the case of the first illumination angle a, an illumination angle relative to the photographing optical axis can be selected in the range of about 60 to 70°, as shown by symbols p to q, and in the case of the second illumination angle b, an illumination angle relative to the photographing optical axis can be selected in the range of about 14 to 16°, as shown by symbols r to s.

It would be structurally impractical to provide a dark field illumination having such a range without the use of the half mirror 215. For example, if an illumination angle range such as b were to be obtained using the structure in FIG. 1, it would be necessary to dispose the LED 231 at the location shown by symbol A under the half mirror 215 in FIG. 1. However, this would be undesirable since shading would occur in the photographing optical system. It would thus be necessary to actually dispose the LED 231 in the photographing optical system farther away so that the LED 231 could be placed outside the photographing optical system. This makes the structure larger.

In the present embodiment, the half mirror 215 can be pivoted and fixed at minute angles using the spindle 215a, thereby making it possible to adjust the illumination angle of the low-angle dark field illumination light sources 221b and 221c of the fixed LED 221 within a diverse range of illumination angles. The half mirror 215 is also used in the second illumination angle for illuminating the object O, thus making it possible to select an illumination angle within a range of angles even greater than above.

Thus, in cases, for example, where the visibility of the image of an object O read by the imaging device 211 is poor or there are problems such as in the recognition efficiency of OCR processing or the like, the nuts 242, 242 and screws 241, 241 can be loosened to select the first illumination angle a or second illumination angle b, and to micro-adjust each illumination angle so as to obtain more suitable image reading results.

According to the present embodiment, the reflection of the half mirror 215, which is arranged for bright field to low-angle dark field illumination applications, can be used to realize illumination having two completely different variable angle ranges using a single illumination light source. In the present embodiment, the base plate 231a on which the LED 231 is mounted is also supported by a swing-type support member 250 having arms 244, 244 of a certain length. The fixing angle and fixing location of the support member 250 can furthermore be micro-adjusted using the long holes 243, 243. A variable range of angles of incidence can therefore be realized using members or components whose movable range is as small as possible, and the components of the housing 203 will not be needlessly enlarged.

As described above, in the present embodiment, the angle and position at which at least one illumination light source is attached can be varied, thereby making it possible to continuously change the illumination angle of incidence within a certain range. The range of the angles of incidence at such times is determined by the variable range of the illumination light source and the positional relationship to the object. However, the reflection of the half mirror 215 or a ring-shaped mirror instead of the half mirror 215 can be further used or the rotational angle thereof can be adjusted. This provides the exceptional effects to realize two or more different ranges of diverse angles of incidence with a single illumination light source and makes it possible to vastly increase the chances of obtaining captured images of desirable picture quality.

What is claimed is:

1. An optical reader having an imaging device and a photographing optical system for reading images of an object, the optical reader comprising:
   a dark field illumination light source for illuminating the object at an angle of illumination that deviates from the optical axis of the photographing optical system;
   reflection means for reflecting the illuminating light from the dark field illumination light source in the direction of the object; and
   adjustment means for adjusting the angle and position of the dark field illumination light source so as to provide either a first angle of illumination for directly illuminating the object with the illuminating light of the dark field illumination light source, or a second angle of illumination for illuminating the object by reflection via the reflection means.

2. An optical reader according to claim 1, wherein the reflection means is disposed in an illumination optical system that is disposed near the photographing optical system and includes an illumination light source different from the dark field illumination light source.

3. An optical reader according to claim 2, wherein the illumination optical system that includes the illumination light source different from the dark field illumination light source is a bright field illumination optical system.

4. An optical reader according to claim 2, wherein the illumination optical system that includes the illumination light source different from the dark field illumination light source includes a bright field illumination light source and a low-angle dark field illumination light source.

5. An optical reader according to claim 4, wherein the low-angle dark field illumination light source comprises a first low-angle dark field illumination light source in which the angle of incidence with the optical axis is 1° to 3°, and a second low-angle dark field illumination light source in which the angle of incidence with the optical axis is 3° to 5°.

6. An optical reader according to claim 1, further comprising means for adjusting the angle of reflection of the reflection means.

* * * * *